(12) United States Patent
Munn et al.

(10) Patent No.: US 12,013,593 B2
(45) Date of Patent: Jun. 18, 2024

(54) LENS RETENTION SYSTEM

(71) Applicant: Fox Head, Inc., Irvine, CA (US)

(72) Inventors: David Munn, Irvine, CA (US); Michael Peters, Irvine, CA (US)

(73) Assignee: Fox Head, Inc., Irvine, CA (US)

( * ) Notice: Subject to any disclaimer, the term of this patent is extended or adjusted under 35 U.S.C. 154(b) by 781 days.

(21) Appl. No.: 16/714,487

(22) Filed: Dec. 13, 2019

(65) Prior Publication Data
US 2021/0048684 A1 Feb. 18, 2021

Related U.S. Application Data

(60) Provisional application No. 62/886,336, filed on Aug. 13, 2019.

(51) Int. Cl.
*G02C 1/00* (2006.01)
*A61F 9/02* (2006.01)

(52) U.S. Cl.
CPC .............. *G02C 1/10* (2013.01); *A61F 9/025* (2013.01); *A61F 9/026* (2013.01); *G02C 2200/08* (2013.01)

(58) Field of Classification Search
CPC ....... G02C 1/10; G02C 2200/08; A61F 9/025; A61F 2009/021; A61F 9/022; A61F 9/02; A61F 9/026
See application file for complete search history.

(56) References Cited

U.S. PATENT DOCUMENTS

| 3,505,680 | A | * | 4/1970 | Ring | A61F 9/025 2/435 |
| 6,463,590 | B1 | * | 10/2002 | Dean | A61F 9/025 2/424 |
| 2004/0025232 | A1 | * | 2/2004 | Hartley | A61F 9/025 2/452 |
| 2009/0100577 | A1 | * | 4/2009 | Kobayashi | A61F 9/02 2/435 |
| 2012/0137414 | A1 | * | 6/2012 | Saylor | B32B 27/00 428/80 |
| 2018/0042773 | A1 | * | 2/2018 | Boinnard | A61F 9/029 |

* cited by examiner

*Primary Examiner* — Nathan E Durham
*Assistant Examiner* — Abby M Spatz
(74) *Attorney, Agent, or Firm* — Reed Smith LLP; Walter M. Egbert, III; Richard J. Brown

(57) ABSTRACT

A frame for an eyewear comprises a lens opening and a groove surrounding the lens opening. The lens opening may be defined by an upper frame portion, a lower frame portion, a first lateral side portion, and a second lateral side portion of the frame. The groove may interchangeably receive and secure a first lens and a second lens within the lens opening. The first lens may have a different thickness than the second lens. The lens opening may extend across both eyes of the wearer.

11 Claims, 15 Drawing Sheets

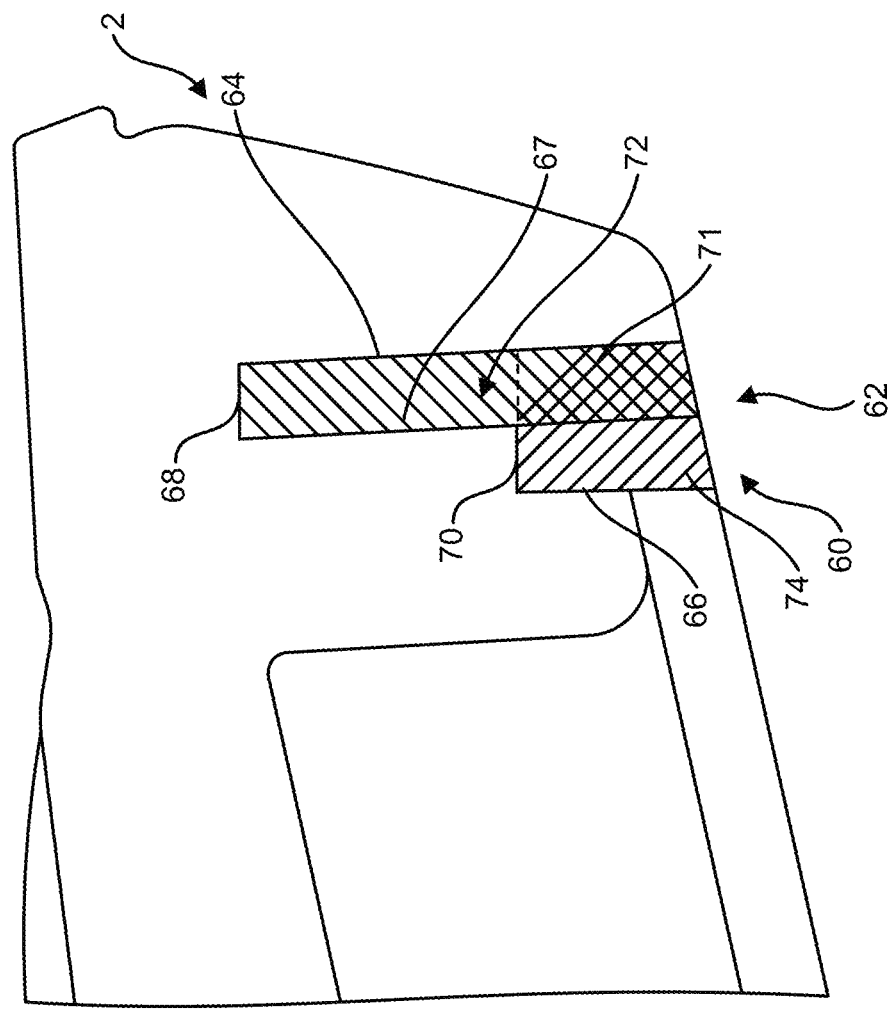

LENS RETENTION SYSTEM

CROSS-REFERENCE TO RELATED APPLICATIONS

The present application claims priority to U.S. Provisional Application No. 62/886,336, filed on Aug. 13, 2019, and titled "LENS RETENTION SYSTEM," the entirety of which is incorporated by reference herein.

BACKGROUND

The subject matter disclosed herein generally relates to a lens retention system (e.g., a coupling system, an outrigger locking system, a quick release system, etc.). The lens retention system can couple one or more types of lenses to and/or within a frame of eyewear (e.g., goggles, glasses, sunglasses, protective eyewear, helmets, and the like). The lens retention system may be used in conjunction with protective helmets or other protective gear for sports or vocations.

Eyewear, such as goggles, glasses, sunglasses, etc., often include one or more lenses that are disposed within a frame of the eyewear to hold the lenses in place. Such an arrangement may make it difficult to interchange and/or replace lenses. Each of the lenses may also have one or more types of geometries (e.g., widths, shapes, sizes, and the like), materials, or other properties, which also may make it difficult to interchange and/or replace lenses.

SUMMARY

According to some embodiments, a frame for an eyewear is provided. The frame can include a lens opening and a groove surrounding the lens opening. The lens opening may be defined by an upper frame portion, a lower frame portion, a first lateral side portion, and a second lateral side portion. The lens opening may extend across both eyes of a wearer. The groove may surround the lens opening. The groove may receive and secure a first lens and a second lens within the lens opening. The first lens may have a different thickness than the second lens.

In some embodiments, the groove includes a first lens receiving portion and a second lens receiving portion. The first lens receiving portion may receive the first lens. The first lens receiving portion may define a first receiving volume. The second lens receiving portion may receive the second lens. The second lens receiving portion may define a second receiving volume. The first receiving volume may overlap with the second receiving volume. In some embodiments, the first lens receiving portion may include an outer groove wall, an intermediate groove wall having a depth that is less than a depth of the outer groove wall, and a first platform extending between a first end of the outer groove wall and a first end of the intermediate groove wall.

In some embodiments, the second lens receiving portion includes an inner groove wall, the outer groove wall, and a second platform extending between a first end of the inner groove wall and a second end of the intermediate groove wall. The second end of the intermediate groove wall may be positioned opposite the first end of the intermediate groove wall. In some embodiments, the first lens receiving portion has a first depth and a first thickness. The second lens receiving portion may have a second depth and a second thickness. The first depth may be greater than the second depth. The first width is less than the second width. In some embodiments, the first lens has one or more different properties than the second lens, such as rigidity and material.

According to some embodiments, an eyewear system includes a first lens having a first thickness, a second lens having a second thickness different than the first thickness, and a frame. The frame may include a lens opening defined by an upper frame portion, a lower frame portion, a first lateral side portion, and a second lateral side portion. The lens opening may extend across both eyes of the wearer. The frame may also include a groove surrounding the lens opening. The groove may receive and secure the first lens within the lens opening. The groove may receive and secure the second lens within the lens opening.

According to some embodiments, a method of providing an eyewear includes providing a first lens to a frame. The first lens may have a first thickness. The frame may include a lens opening defined by an upper frame portion, a lower frame portion, a first lateral side portion, and a second lateral side portion. The lens opening may extend across both eyes of the wearer. The frame may also have a groove surrounding the lens opening. The method may also include removing the first lens from the frame. The method may also include providing a second lens to the frame. The second lens may have a second thickness that is different from the first thickness. In some embodiments, providing the first lens includes positioning the first lens within a first lens receiving portion of the frame. The first lens receiving portion may define a first receiving volume. In some embodiments, the method includes positioning the second lens within a second lens receiving portion of the frame. The second lens receiving portion may define a second receiving volume. The first receiving volume may overlap with the second receiving volume.

According to some embodiments, a method of securing lenses of different structure to an eyewear frame is provided. The method includes providing a frame. The frame may include a lens opening defined by an upper frame portion, a lower frame portion, a first lateral side portion, and a second lateral side portion. The lens opening may extend across both eyes of a wearer. The frame may also include a groove surrounding the lens opening. The groove may interchangeably receive and secure a first lens and a second lens within the lens opening. The groove may include a first depth, a second depth, a first width, and a second width. The first depth and the first width may correspond to a thickness and/or depth of one of the first lens and the second lens, and the second depth and the second width may correspond to the thickness and/or depth of one of the first lens and the second lens. The method may also include securing either of the first lens and the second lens to the frame by inserting a portion of the first lens and second lens into the groove. The first lens may have a different thickness and/or depth than the second lens.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings:

FIG. 13 is a close-up view of a lens retention system of an eyewear according to some example embodiments.

DETAILED DESCRIPTION

Figure 1:
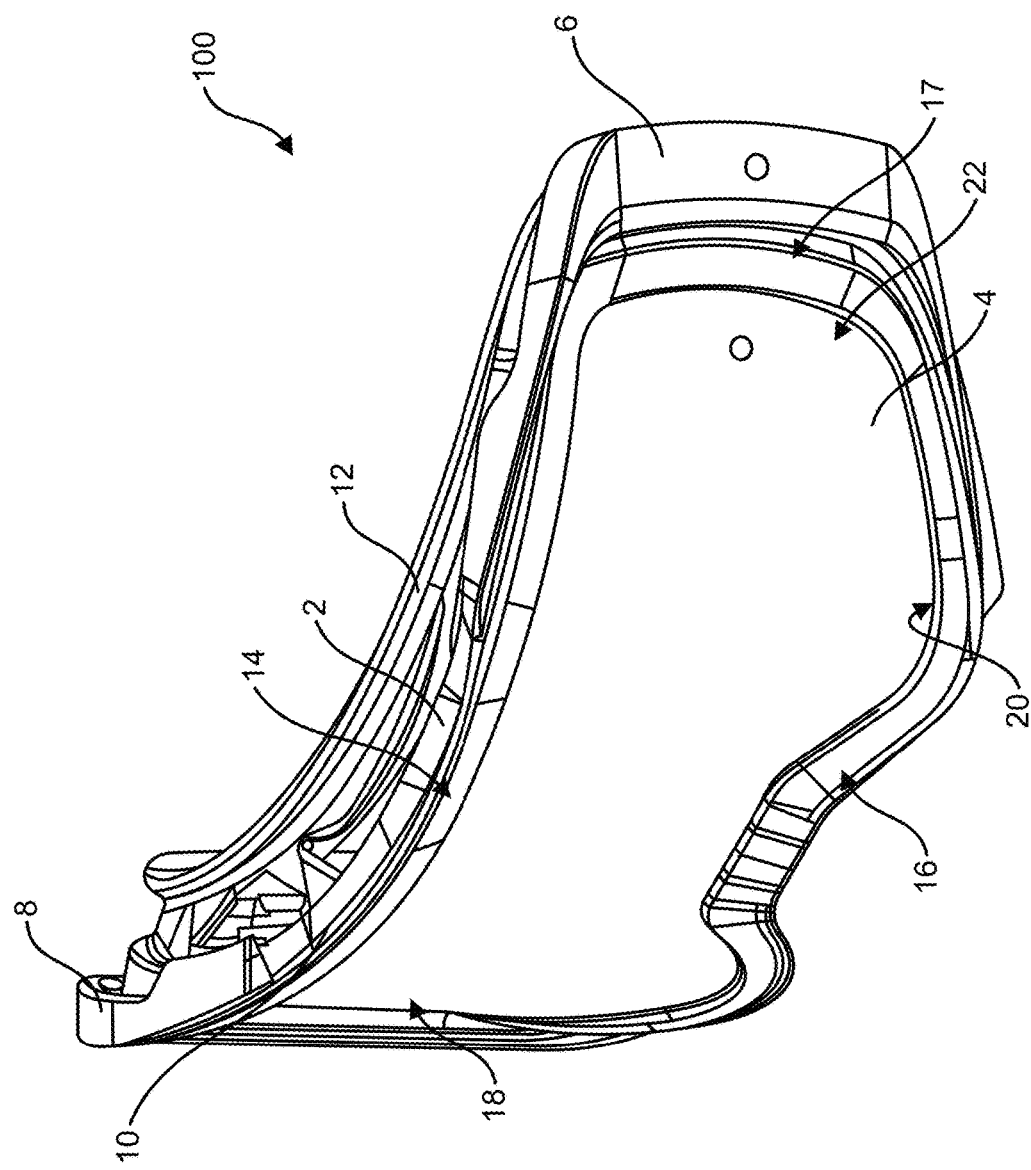
FIG. 1 is a perspective view of an eyewear according to some example embodiments.
Figure 2:
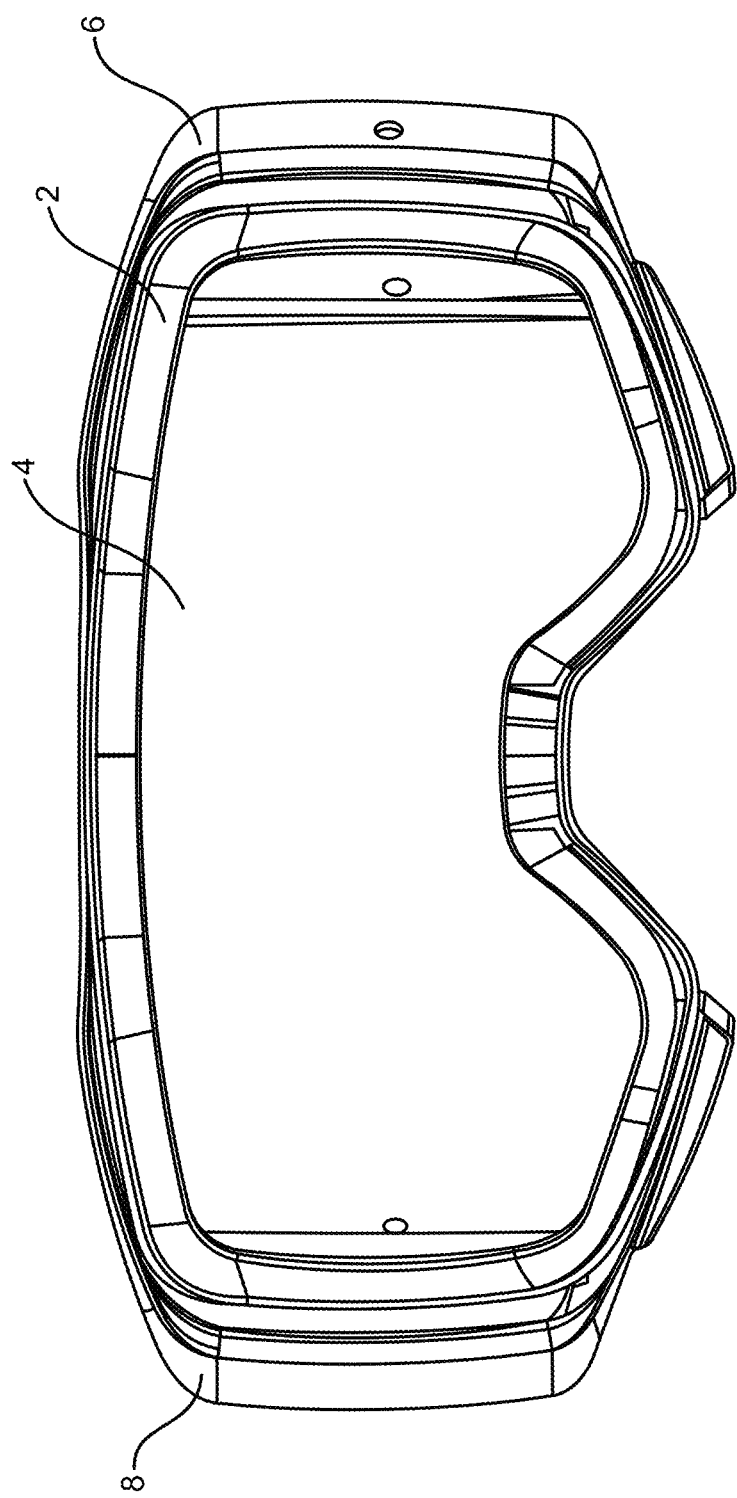
FIG. 2 is a front view of an eyewear according to some example embodiments.
Figure 3:
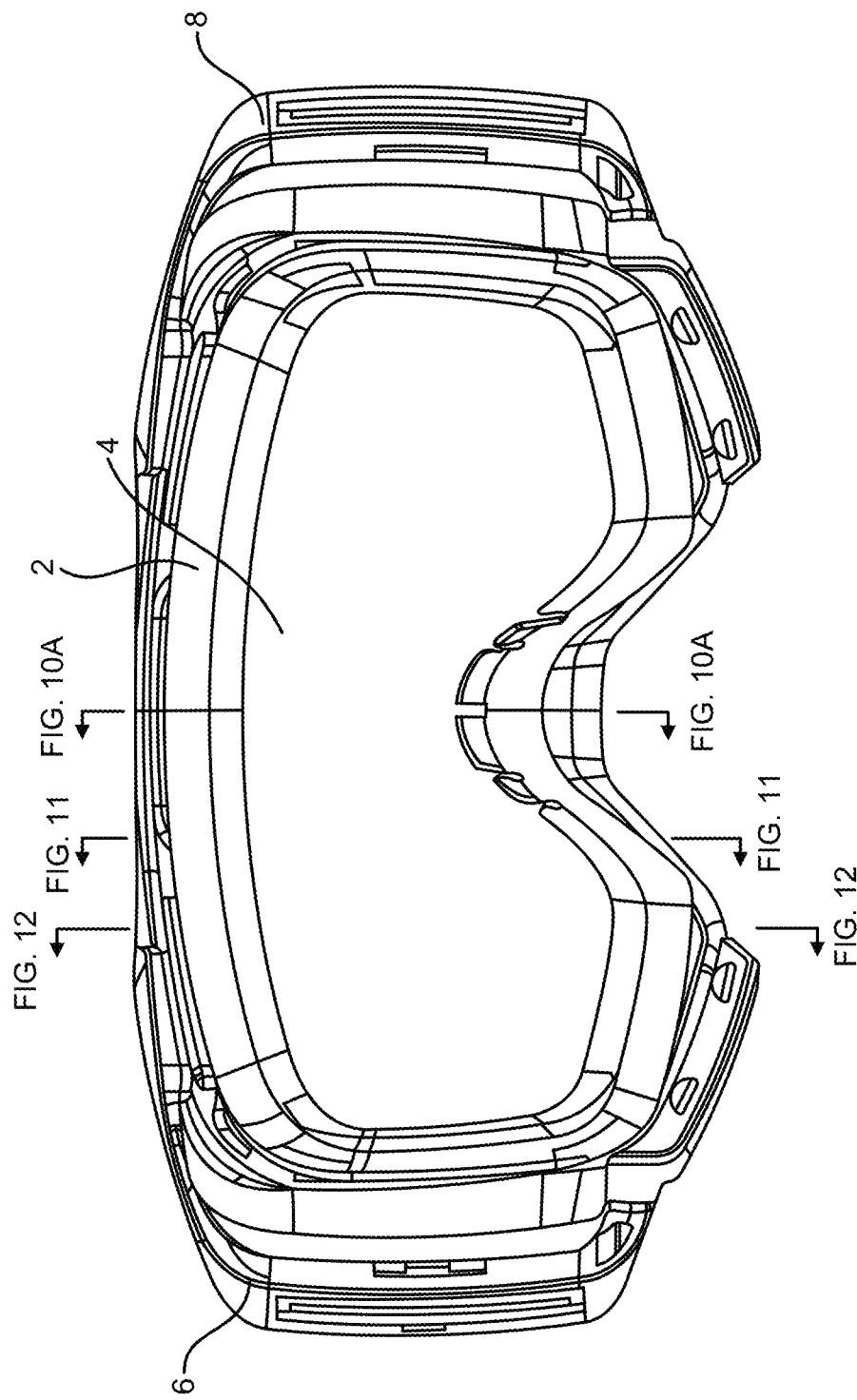
FIG. 3 is a rear view of an eyewear according to some example embodiments.

Various aspects of the disclosure will now be described with regard to certain examples and embodiments, which are intended to illustrate but not to limit the disclosure. Nothing in this disclosure is intended to imply that any particular feature or characteristic of the disclosed embodiments is essential. The scope of protection is defined by the claims that follow this description and not by any particular embodiment described herein. Before turning to the figures, which illustrate example embodiments in detail, it should be understood that the application is not limited to the details or methodology set forth in the description or illustrated in the figures. It should also be understood that the terminology is for the purpose of description only and should not be regarded as limiting.

Embodiments herein generally relate to a lens retention system (e.g., a coupling system, an outrigger locking system, a quick release system, etc.). The lens retention system can couple one or more types of lenses to and/or within a frame of eyewear (e.g., goggles, glasses, sunglasses, protective eyewear, helmets, and the like). The lens retention system may facilitate coupling and/or retaining the lens to the frame in a relatively simple (e.g., easy, quick, etc.) and/or toolless manner (e.g., does not require the use of tools, such as a screw driver, or other tool). Such eyewear may be used in a number of activities, such as sports and athletics, including extreme sports such as motocross and snowmobiling; cycling activities, including auto racing, motorcycle riding and racing, BMX, mountain biking, and the like; with recreational vehicles including all-terrain vehicles (ATVs), dirt bikes, utility task vehicles (UTVs), snowmobiles, and other off-road vehicles; military applications; and/or construction applications, and the like.

Generally, a wearer may partake in various activities that require the use of different types of lenses. For example, during some activities, a wearer may use one type of lens, such as a cheaper, lower quality, thin, and/or flexible lens made out of various materials (e.g., stamped lenses made of polycarbonate, and the like). While performing other activities, however, the wearer may use another type of lens, such as a more expensive, higher quality, thicker, and/or rigid lens made out of other materials (e.g., injection molded polycarbonate lenses, and the like). However, many types of eyewear may only support a single type of lens. Thus, the wearer may need to purchase and use multiple types of eyewear to be able to support each type of lens the wearer wishes to use. The wearer may also need to carry multiple eyewear (e.g., frames), which may be bulky or otherwise be difficult depending on what the wearer is doing.

In some examples, such as when the wearer only has eyewear that supports the more expensive, higher quality, thicker, and/or rigid lens, the wearer may undesirably damage the lens during an activity during which it would have been more beneficial to use the cheaper, lower quality, thin, and/or flexible lens. Implementations of the lens retention system described herein may desirably accommodate multiple types of lenses, such as the lenses described above, thereby allowing for the lenses to be easily interchanged and securely retained within or to a single eyewear. The lens retention system may also provide the wearer with the ability to choose from one or more types of lenses, thereby providing the wearer with lens options for use in various activities. The wearer would also not need to carry multiple frames, which would be less bulky and more lightweight. The wearer would only need to carry a single frame that is capable of accommodating multiple types of lenses.

In some examples, if an improper type of lens is coupled to the eyewear, the lens may become loose, disengage from the eyewear, become damaged, result in poor vision, and the like. Implementations of the lens retention system described herein may desirably accommodate and secure multiple types of lenses, thereby allowing for the lenses to be easily interchanged and securely retained within or to the eyewear without causing damage to the frame or to the lenses. The lens retention system described herein may beneficially enhance the wearer's visibility through the lens, as the lens is securely retained by the eyewear.

FIG. 1 illustrates an example eyewear 100. The eyewear 100 may provide protection to the eyes and adjacent area of the face of the wearer. The eyewear 100 (e.g., frame, lens, etc.) may intercept light, wind, rain, snow, water, particulate matter (e.g., dust, dirt, mud, etc.) and the like to protect the eyes and/or various portions of the face of the wearer of the eyewear 100. In FIG. 1, the eyewear 100 is illustrated in the form of goggles. However, other examples of eyewear are contemplated and may include the same or similar features, such as motocross goggles, snowmobiling goggles, snowboarding goggles, mountain biking goggles, motorcycle goggles, sky diving goggles, or another action or extreme sport goggles, swimming goggles or other sports goggles (e.g., used in basketball, baseball, etc.; Rec Specs®; etc.), other eyewear for construction, military applications, machining, carpentry, scientific experimentation, traditional vision enhancing glasses (e.g., prescription glasses, etc.) and/or sunglasses, and/or the like.

The eyewear 100 includes a frame 2, a lens 4, and first and second outriggers 6, 8. As described in more detail below, the lens 4 may be coupled to and/or otherwise retained by the frame 2 (e.g., the frame may be shaped and/or sized to accommodate the lens 4). For example, the lens 4 may be disposed within, extend across, be supported by, be mounted in, or otherwise coupled to a portion of the frame 2 that surrounds the cavity (e.g., a lens opening) defined by the frame 2. The first and second outriggers 6, 8 may be coupled to the frame 2 and may be configured to couple to a strap, helmet (e.g., football helmet, hockey helmet, lacrosse helmet, welding helmet, motorcycle helmet, and the like), visor, or other device that allows the eyewear 100 to be worn by the wearer.

The frame 2 may be substantially rigid, which may help to improve optical clarity for the wearer. The frame 2 may be made of one or more materials, such as Nylon, TPU, EVA, among others. The frame 2 includes an outer frame portion 10 configured to face away from the wearer and an inner frame portion 12 configured to contact or otherwise face towards the wearer when worn. The frame 2 may also include a cushion member that is configured to contact the wearer.

The inner frame portion 12 may be shaped to correspond with anatomical features of a wearer's face (e.g., cheeks, nose, forehead, and the like) to facilitate a proper fit of the eyewear 100 when worn. The inner frame portion 12 may include an impact attenuating material and/or cushion material (e.g., expanded polyurethane (EPU) foam, expanded polypropylene (EPP) foam, expanded polyethylene (EPE) foam, polyolefin foam, etc.) to facilitate a snug and comfortable fit of the eyewear 100 onto the wearer's face, for example, to mitigate impact forces encountered by the eyewear 100 (e.g., from flying debris, etc.).

The outer frame portion 10 may be positioned along or spaced apart from the inner frame portion 12. According to some embodiments, the outer frame portion 10 facilitates coupling the lens 4 to the frame 2 via the lens retention system 60.

As shown in FIGS. 1-13, the outer frame portion 10 has an upper frame portion 14, a lower frame portion 16, a first lateral frame portion 17, and an opposing second lateral frame portion 18. The upper frame portion 14, the lower frame portion 16, the first lateral frame portion 17, and the second lateral frame portion 18 may be integrally formed. The upper frame portion 14, the lower frame portion 16, the first lateral frame portion 17, and the second lateral frame portion 18 cooperatively define a cavity therebetween, shown as a lens opening 22. The lens opening 22 is configured to receive the lens 4. The lens opening 22 may extend across both eyes of the wearer.

As discussed in more detail below, the frame 2 is configured to accommodate and retain at least one (e.g., at least two, three, or more) types of lenses 4 (e.g., various types of lens geometries). Each of the lenses 4 may form a unitary, arcuate lens that extends across the lens opening 22 (e.g., both the left and right eyes of the wearer, etc.). For example, the lens 4 may extend from the first lateral frame portion 17 to the second lateral frame portion 18 when the lens 4 is coupled to the frame 2. In some alternative embodiments, the lens 4 includes dual lenses, one positioned over each of the left and right eyes of the wearer. In some embodiments, the lens 4 is clear (e.g., substantially transparent). In other embodiments, the lens 4 includes a tinted and/or polarized coating to shade a wearer's eyes from sunlight, reduce glare, improve contrast, and/or enhance depth perception. The tinted and/or polarized coating may be various colors (e.g., black, yellow, blue, green, brown, gray, red, etc.). In some embodiments, the lens 4 includes a reflective coating (e.g., to prevent others from seeing where the wearer is looking, etc.). In some embodiments, the lens 4 is a prescription lens configured to enhance the vision of a wearer of the eyewear 100.

The lens 4 may include a first surface 24, an opposing second surface 26, a first edge 28, an opposing second edge 30, a first end (e.g., a first flange) 32, and an opposing second end (e.g., a second flange) 34. The first flange 32 may be shaped to correspond with the first lateral frame portion 17 of the outer frame portion 10 and the second flange 34 may be shaped to correspond with the second lateral frame portion 18 of the outer frame portion 10.

Figure 4:
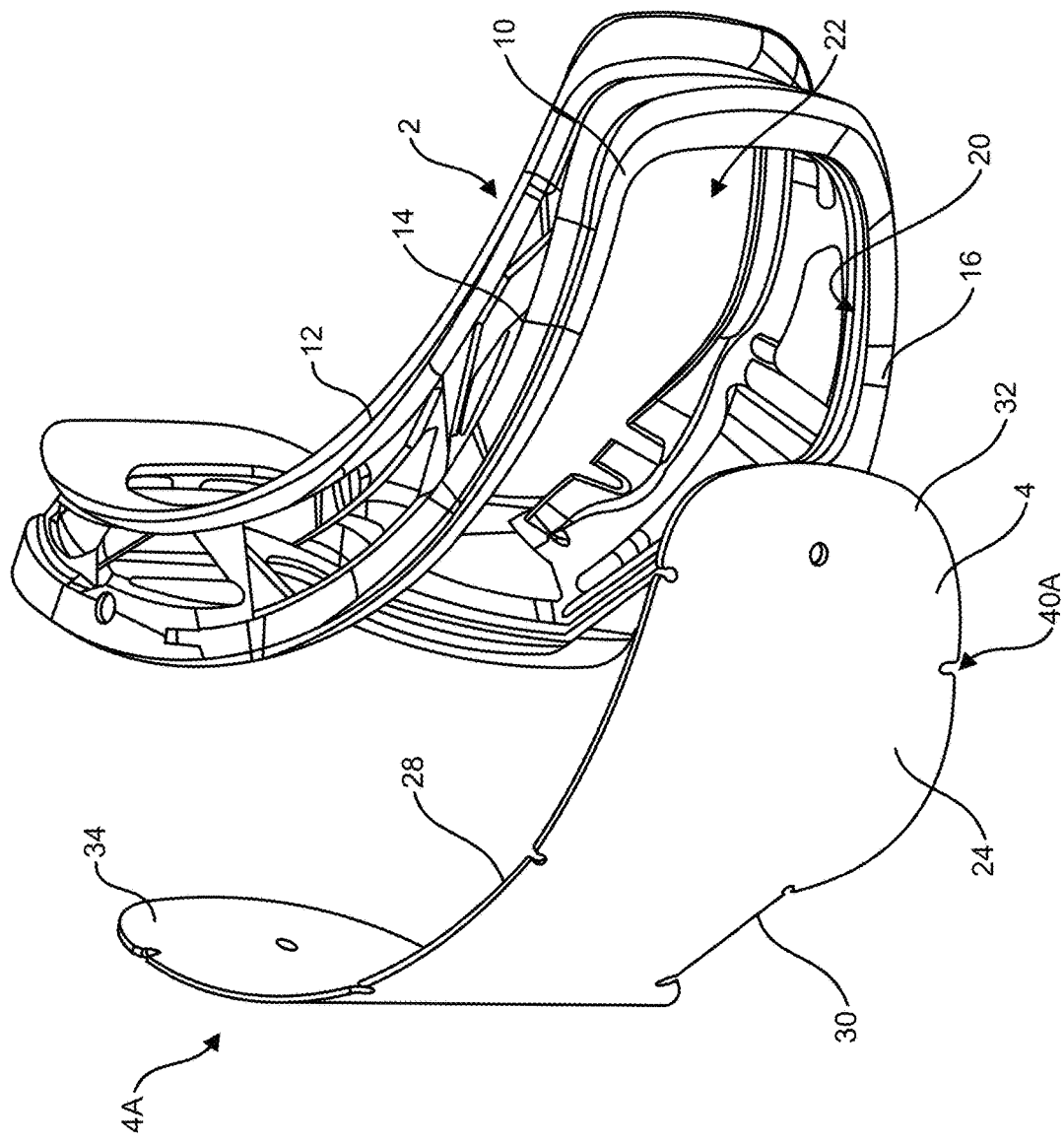
FIG. 4 is an exploded view of an eyewear according to some example embodiments.
Figure 5A:
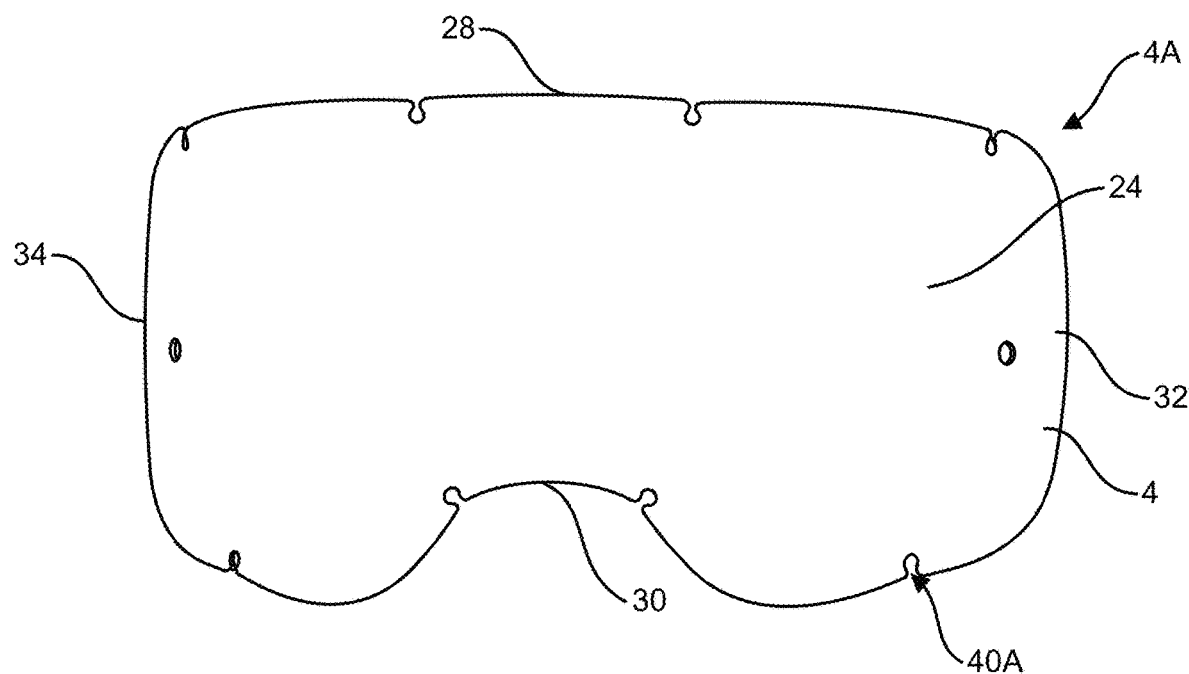
FIG. 5A is a front view of a lens of an eyewear according to some example embodiments.
Figure 5B:
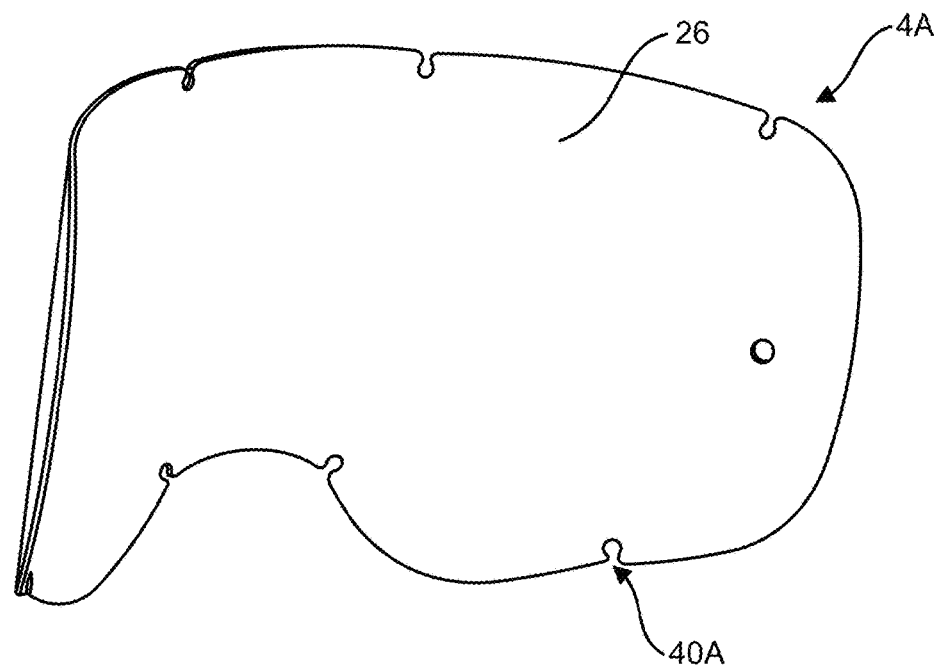
FIG. 5B is a rear perspective view of a lens of an eyewear according to some example embodiments.

FIGS. 4-5B illustrate a lens 4, such as a first lens 4A that may be accommodated and/or otherwise coupleable to the frame 2. In some embodiments, the first lens 4A represents a first type of lens 4. The first lens 4A may be made of a stamped sheet of polycarbonate, among other materials. The first lens 4A may be relatively inexpensive, low quality, thin, and/or flexible. The first lens 4A may have a uniform or variable thickness.

As shown in FIGS. 4-5B, in some embodiments, the first lens 4A (or any of the lenses 4 described herein) has at least one coupling receiver 40A. In some embodiments, the first lens 4A has two, four, six, eight or more coupling receivers 40A. The coupling receiver 40A may be configured to mate with a corresponding coupler 50 located on the frame 2. The coupling receiver 40A may define a cutout in the first lens 4A. The cutout may extend from an outer edge of the first lens 4A inwardly into the first lens 4A. The cutout may be cylindrical, circular, square, rectangular, or triangular, among other shapes. The coupling receivers 40A may be positioned along the first and/or second edges 28, 30 of the first lens 4A, or other portions of the first lens 4A. The coupling receivers 40A may assist in securing or otherwise retaining the lens 4 to the frame 2. For example, the coupling receiver 40A may help to provide an improved fit that secures the lens 4 to the frame 2. In some embodiments, the lens 4 does not have a coupling receiver, such as the coupling receiver 40A, and is secured to the frame 2 by the lens retention system alone.

Figure 6:
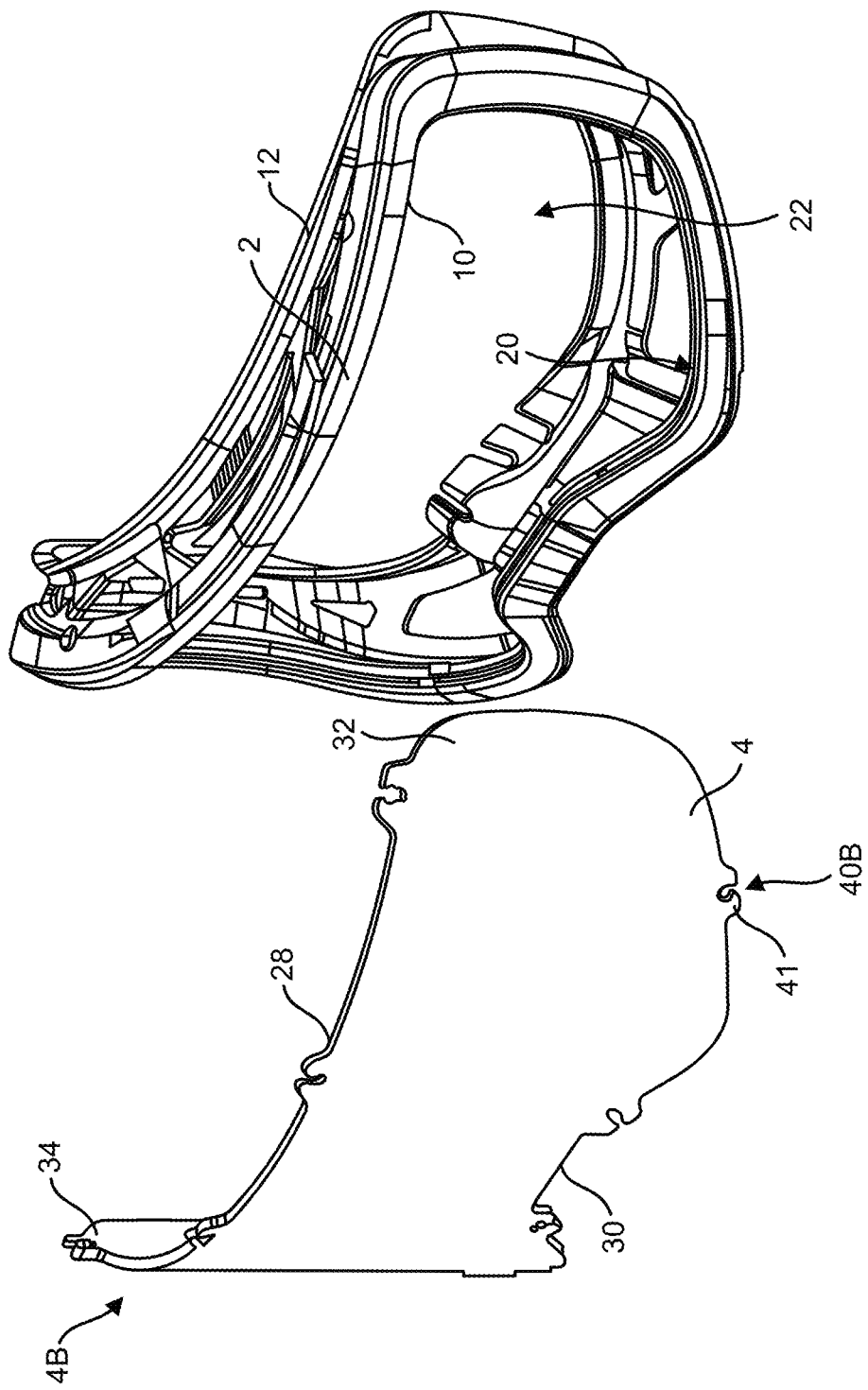
FIG. 6 is an exploded view of an eyewear according to some example embodiments.
Figure 7A:
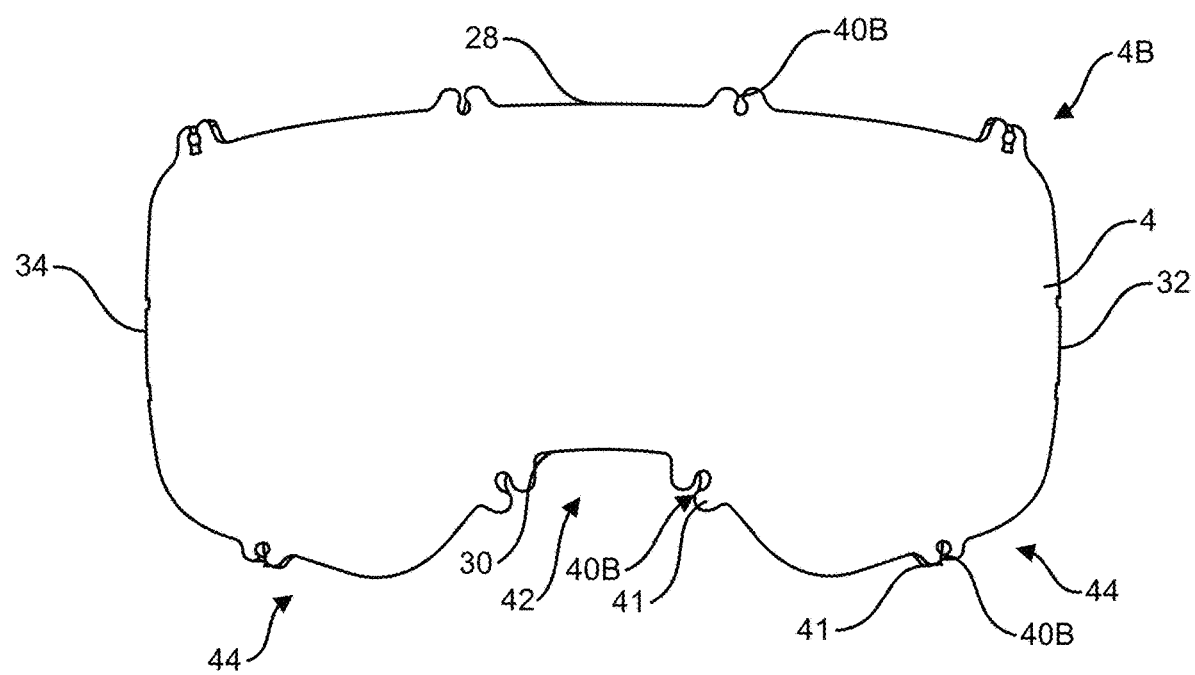
FIG. 7A is a front view of a lens of an eyewear according to some example embodiments.
Figure 7B:
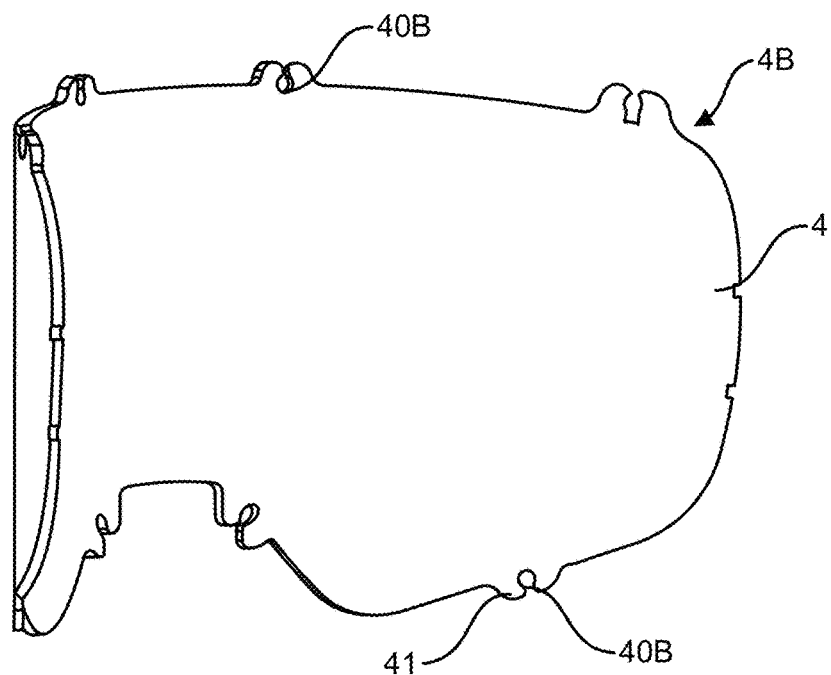
FIG. 7B is a rear perspective view of a lens of an eyewear according to some example embodiments.
Figure 8:
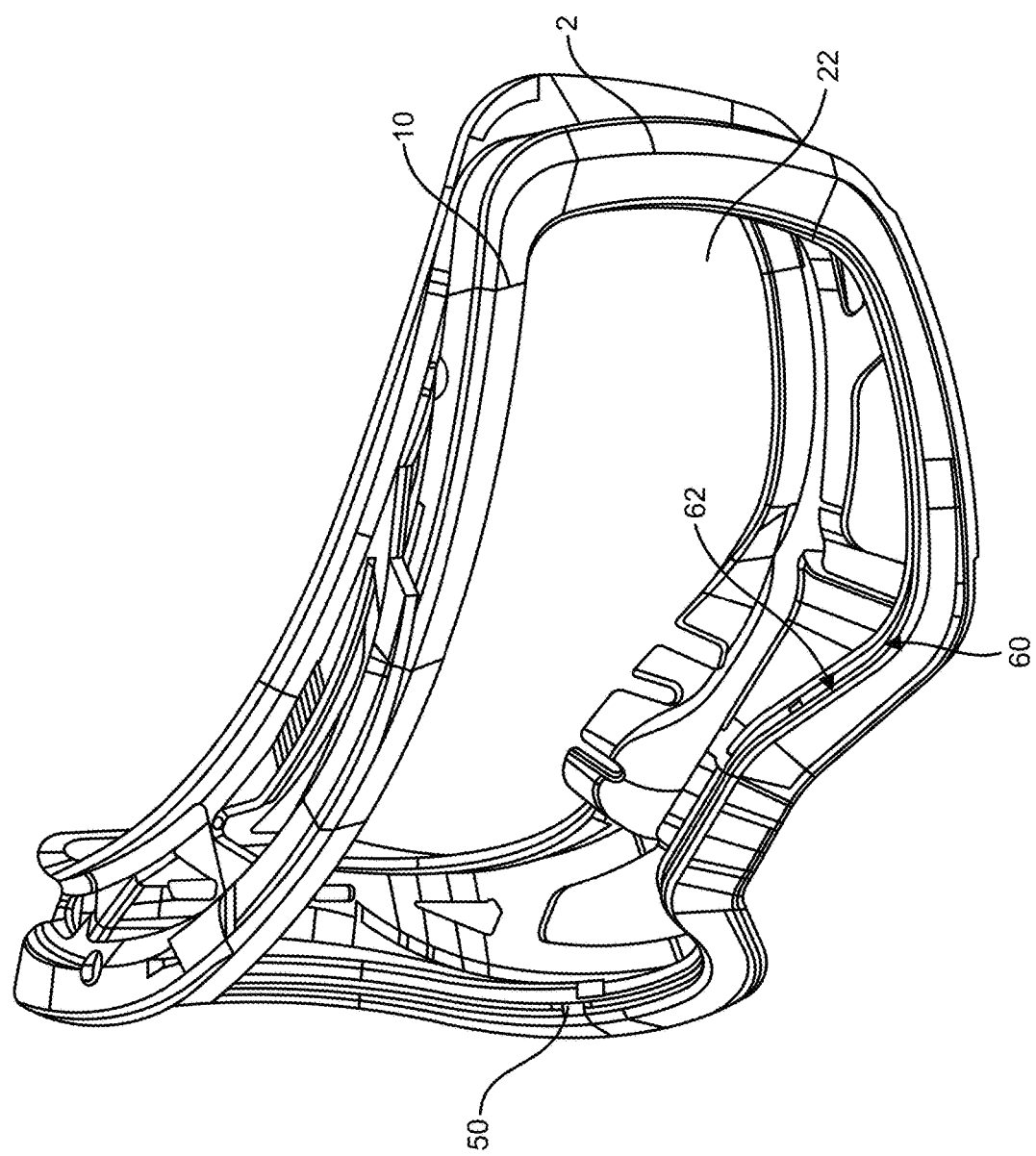
FIG. 8 is a perspective view of a frame of an eyewear according to some example embodiments.
Figure 9:
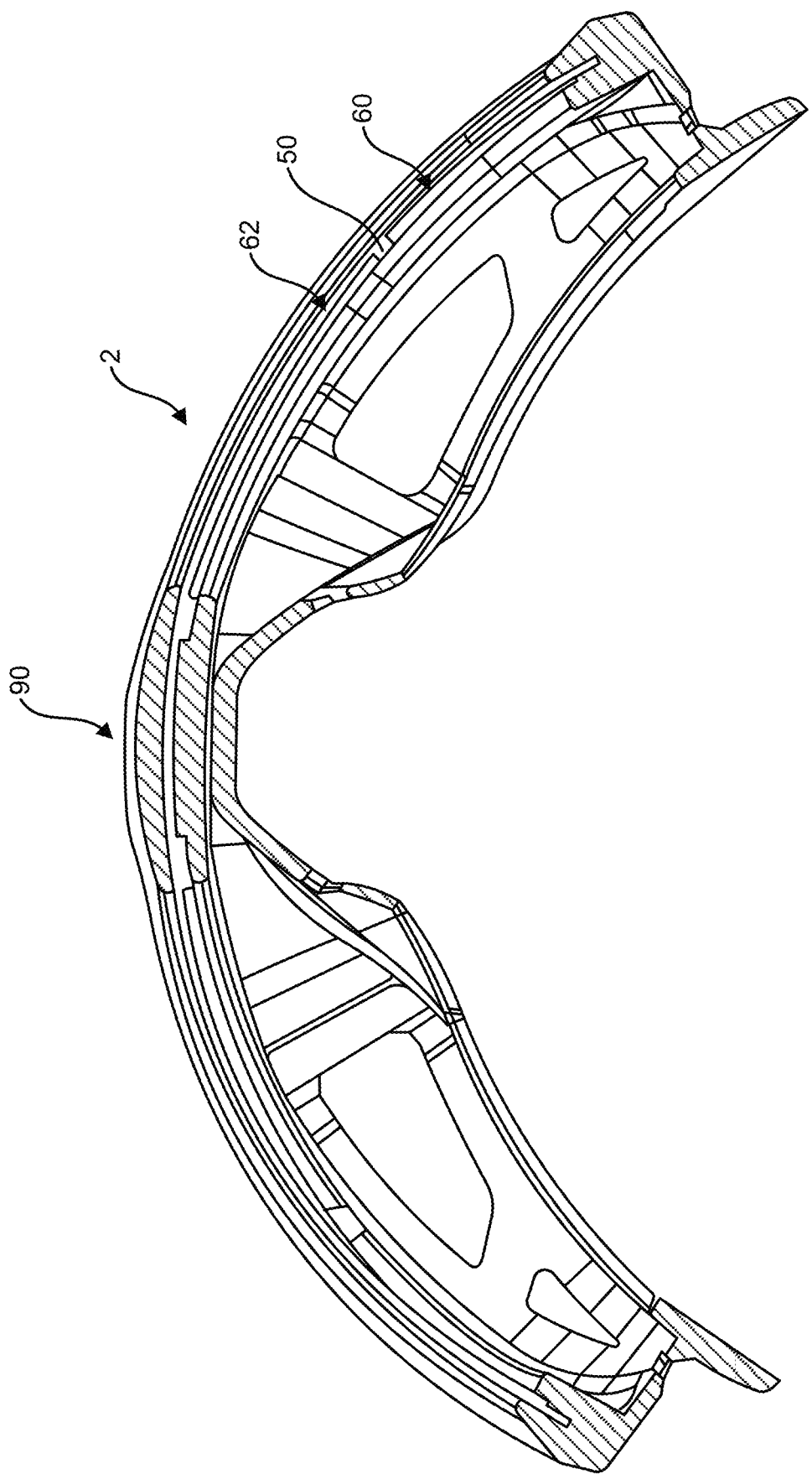
FIG. 9 is a top cross-sectional view of a frame of an eyewear according to some example embodiments.

FIGS. 6-7B illustrates a lens 4, such as a second lens 4B that may be accommodated and/or otherwise coupleable to the frame 4. In some embodiments, the second lens 4B represents a second type of the lens 4. The second lens 4B may be made of an injection molded polycarbonate, among other materials. The second lens 4B may be relatively expensive (e.g., compared to the first lens 4A), high quality, relatively thick, and/or relatively rigid. The second lens 4B may have a uniform or variable thickness. For example, in some embodiments, the second lens 4B has a greater or lesser thickness near a nasal lens region 42 than at a peripheral lens region 44. Such embodiments can provide better or worse optical clarity to the wearer.

As shown in FIGS. 6-7B, in some embodiments, the second lens 4B (or any of the lenses 4 described herein) has at least one coupling receiver 40B. In some embodiments, the second lens 4B has two, four, six, eight or more coupling receivers 40B. The coupling receiver 40B may be configured to mate with a corresponding coupler 50 located on the frame 2. The coupling receiver 40B may define a cutout in the second lens 4B. As shown in FIGS. 6-7B, the coupling receiver 40B may define cutout in an extension 41 (e.g., a portion of the lens 4B that extends away from an outer edge of the second lens 4B) of the second lens 4B. The cutout may extend from an outer edge of the extension 41 of the second lens 4B inwardly into the second lens 4B. The cutout may be cylindrical, circular, square, rectangular, or triangular, among other shapes. The coupling receivers 40B may be positioned along the first and/or second edges 28, 30 of the second lens 4B, or other portions of the second lens 4B. The coupling receivers 40B may assist in securing or otherwise retaining the lens 4 to the frame 2. For example, the coupling receiver 40A may help to provide an improved fit that secures the lens 4 to the frame 2. In some embodiments, the lens 4 does not have a coupling receiver, such as the coupling receiver 40B and is secured to the frame 2 by the lens retention system alone.

FIGS. 8-13 illustrate an example of the frame 2 consistent with implementations of the current subject matter, which may accommodate and/or retain more than one type of lens 4 (e.g., the first lens 4A and the second lens 4B, among other lens types). As shown in FIGS. 8-13, the frame 2 includes a lens retention system 60. The lens retention system 60 may include various features that assist in accommodating and/or securing more than one type of the lens 4 to the frame 2.

The lens retention system 60 includes a groove 62 that extends around an interior edge of the outer frame portion 10 of the frame 2. In some embodiments, the groove 62 defines a recess in which a portion of the lens 4 can reside. The lens 4 can be secured at least partially within the groove 62 via a friction fit and/or a snap fit arrangement, among other coupling arrangements. The lens retention system 60 beneficially allows for a toolless coupling between the lens 4 and the frame 2.

In some embodiments, as noted above, the lens retention system 60 may accommodate and/or secure more than one type of lens 4 to the frame 2. For example, the groove 62 of the retention system 60 may have various depths and/or thicknesses (e.g., non-uniform depths and/or thicknesses) along the length (or at least a portion of the length) of the groove 62 to accommodate lenses 4 having different thicknesses and material properties. The groove 62 may include a stepped portion in which a first region of the stepped portion is shaped to accommodate a first lens and a second region of the stepped portion is shaped to accommodate a send type of lens. In some embodiments, the groove 62 includes one or more couplers 50 that extend from a surface of the groove 62 and are configured to mate with the corresponding coupling receivers 40A, 40B positioned on the lenses 4A, 4B, respectively. The couplers 50 may be spaced evenly along a length of the groove 62 and/or have variable spacing along a length of the groove. 62. In some embodiments, the couplers 50 are located along portions of the groove 62 to provide better support and/or more stability in certain regions of the groove 62 (or frame 2), such as along lateral peripheries of the lens opening. The coupling receivers 40A, 40B may fit around the couplers 50 via a friction fit, a snap-fit arrangement, and/or the like to further secure the lens 2 to the frame 4. Thus, the lens retention system 60 and the couplers 50 may alone, or in combination, help to better secure the lens 4 to the frame 2.

Figure 10A:
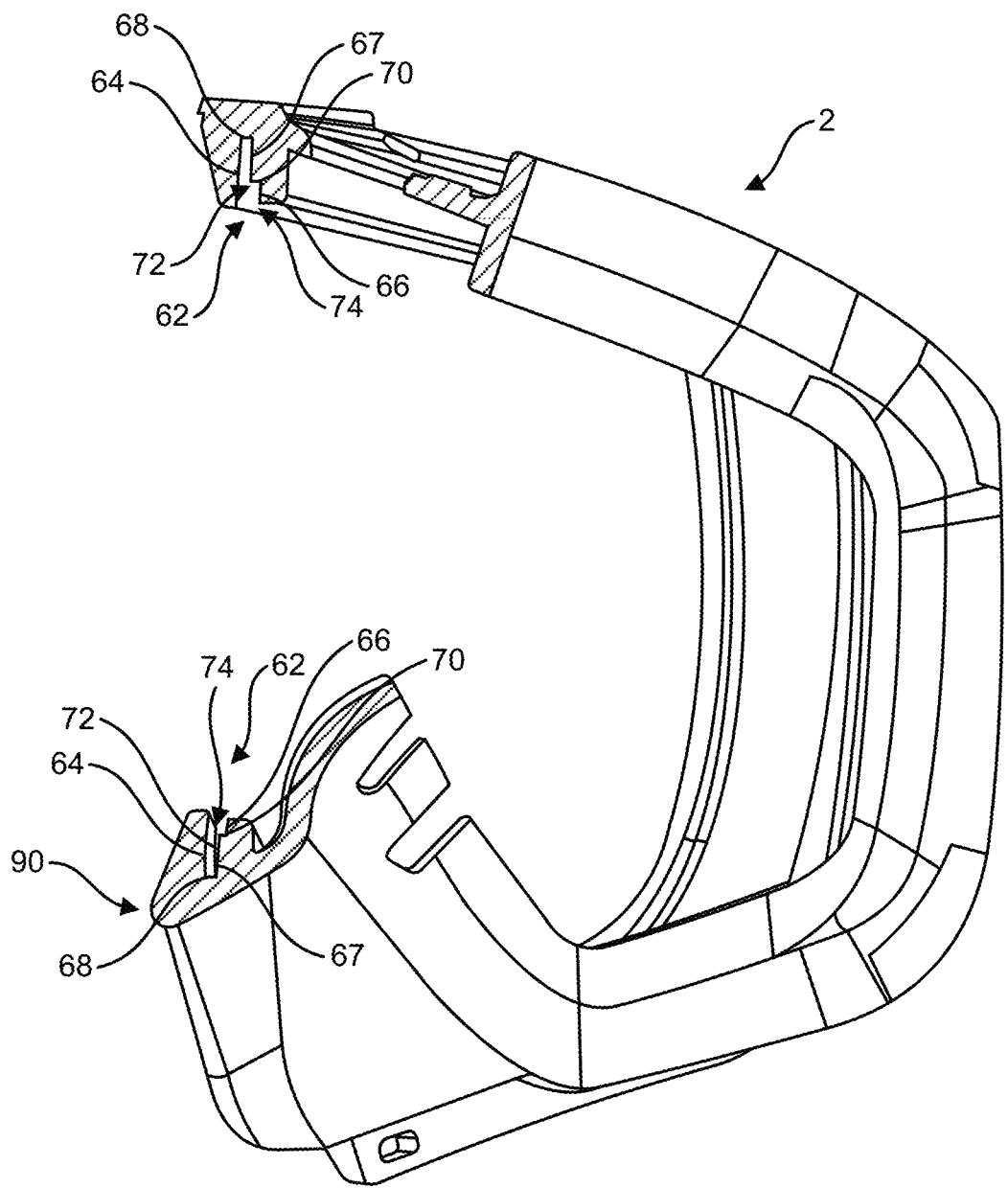
FIG. 10A is a side cross-sectional view of a frame of an eyewear according to some example embodiments.
Figure 10B:
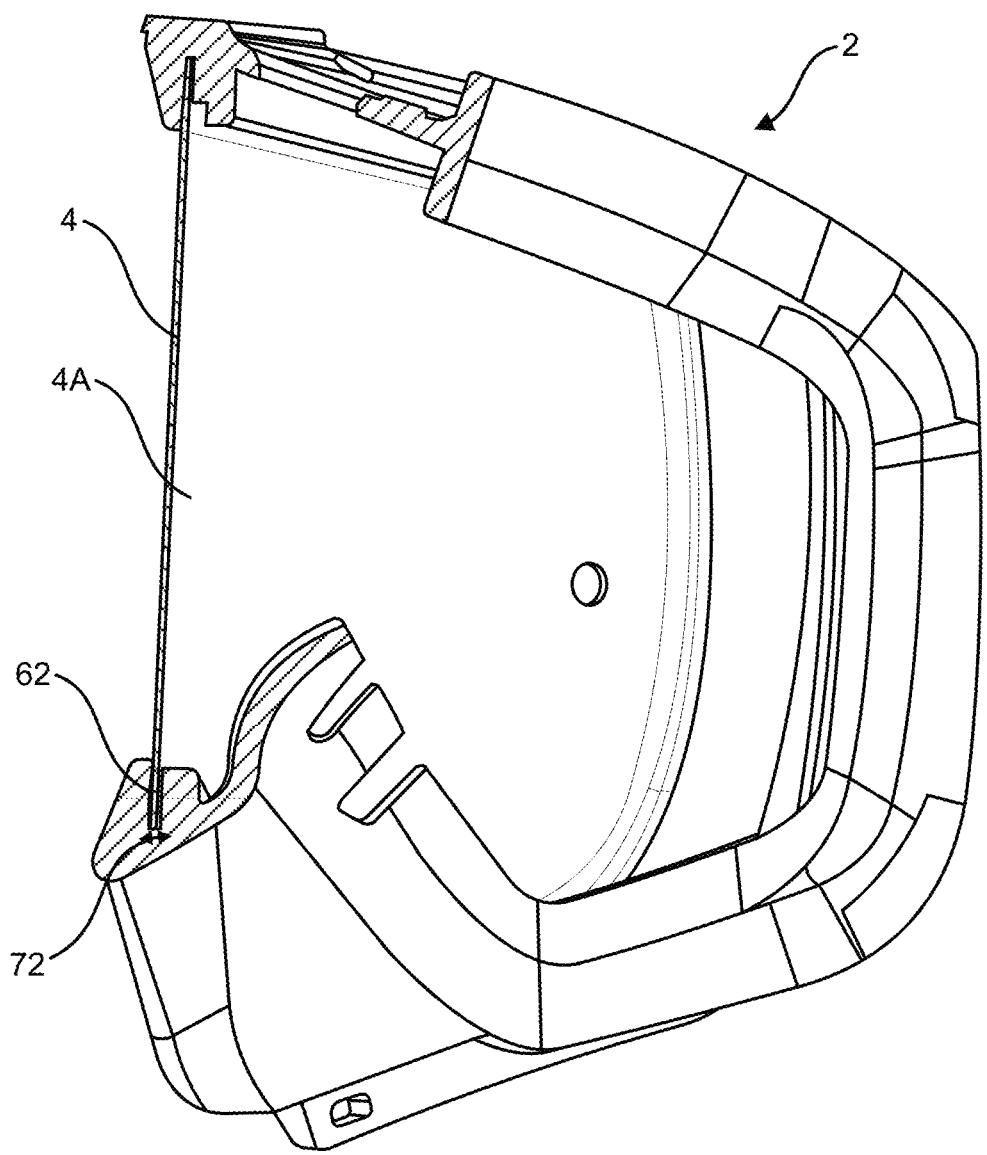
FIG. 10B is a side cross-sectional view of a frame and lens of an eyewear according to some example embodiments.
Figure 10C:
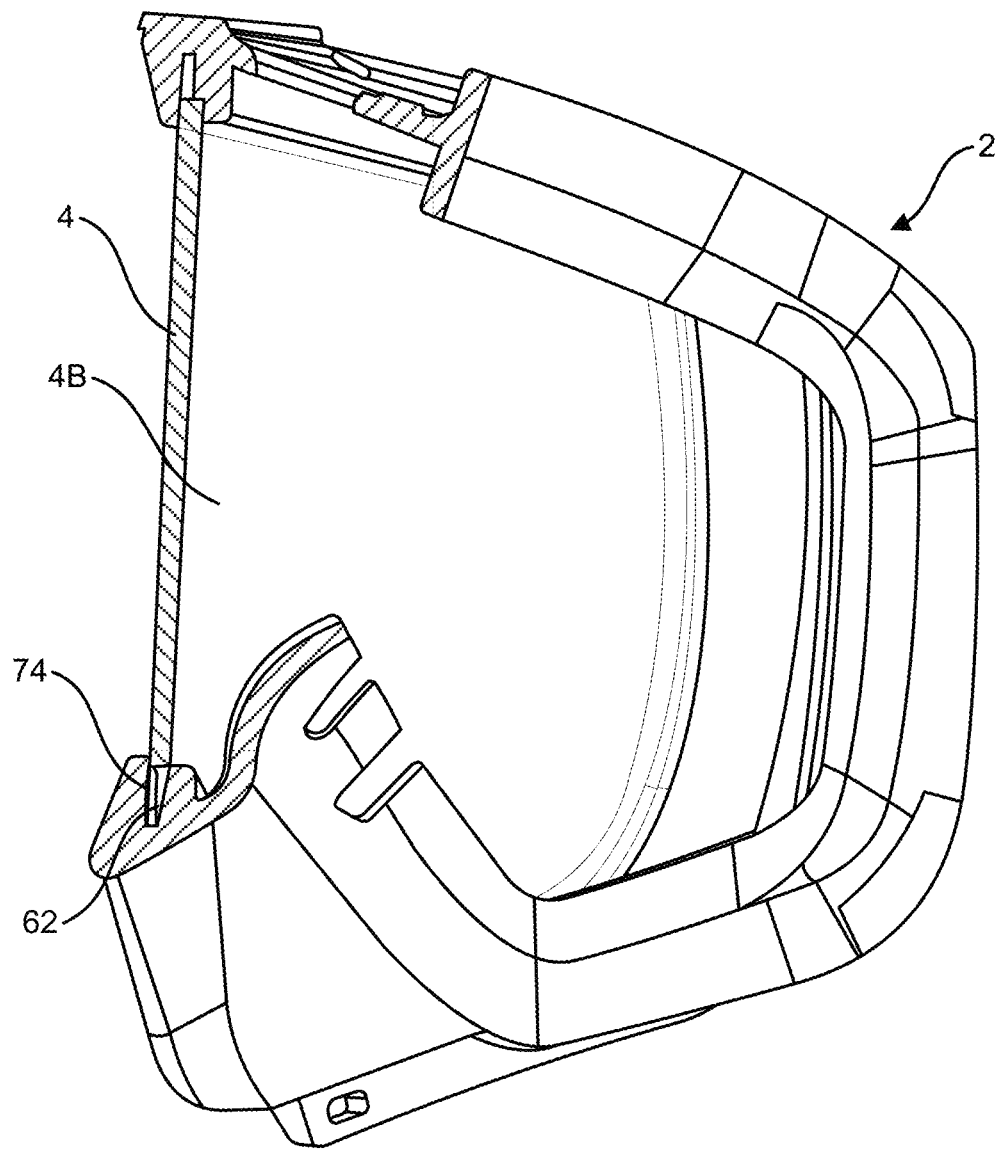
FIG. 10C is a side cross-sectional view of a frame and lens of an eyewear according to some example embodiments.

FIGS. 10A-10C illustrate an example cross-sectional view of the frame 2 along a center of the frame 2 and FIG. 13 illustrates an example close-up view of the lens retention system 60 of an eyewear. As shown in FIGS. 10A and 13, this portion of the frame 2 (e.g., along a nasal region 90 of the frame 2) includes an outer groove wall 64, an inner groove wall 66, an intermediate groove wall 67, a first platform 68, and a second platform 70. The intermediate groove wall 67 may extend from the first platform 68 to the second platform 70. The intermediate roove wall 68 may be perpendicular to both the first and second platforms 68, 70. The first platform 68 may be positioned radially outwardly relative to the second platform 70.

In some embodiments, the first platform 68 has a first width and the second platform 70 has a second width. In some embodiments, the first width of the first platform 68 is less than the second width of the second platform 70 in at least the nasal region of the frame 4.

In some embodiments, the outer groove wall 64 has a first depth and the inner groove wall 66 has a second depth. In some embodiments, the first depth of the outer groove wall 64 may be greater than the second depth of the inner groove wall 66 in at least the nasal region of the frame 4.

In some embodiments, the intermediate groove wall 67 has a third depth that is less than the first depth of the outer groove wall 64. In some embodiments, the first platform 68 extends between a first end of the outer groove wall 64 and a first end of the intermediate groove wall 67. The second platform may extend between a first end of the inner groove wall 66 and a second end of the intermediate groove wall 67. The second end of the intermediate groove wall 67 may be positioned opposite the first end of the intermediate groove wall 67.

In some embodiments, the outer groove wall 64, the intermediate groove wall 67, and the first platform 68 of the groove 62 define a first lens receiving portion 72 that is configured to receive a lens 4 (e.g., the lens 4A), and the inner groove wall 66, the outer groove wall 64, and the second platform 68 of the groove 62 define a second lens receiving portion 74 that is configured to receive another lens 4 (e.g., the lens 4B). In some embodiments the groove 62 includes this configuration along the length, or at least one portion (e.g., adjacent the nasal region 90), of the groove 62. In some embodiments, the first lens receiving portion 72 defines a first receiving volume and the second lens receiving portion 74 defines a second receiving volume. In some embodiments, the first receiving volume overlaps with the second receiving volume. The overlapping volume between the first receiving volume and the second receiving volume may define an overlapping receiving portion 71. The overlapping receiving portion 71 includes a portion of both the first receiving volume and the second receiving volume. In some embodiments, the lens 4, regardless of the lens type, occupies at least the overlapping receiving portion 71 when the lens 4 is coupled to and/or secured within the frame 4.

In some embodiments, the first lens receiving portion 72 has a thickness and/or width (that extends between the intermediate groove wall 67 and the outer groove wall 64) that is less than a thickness and/or width (that extends between the inner groove wall 68 and the outer groove wall 64) of the second lens receiving portion 74. The first lens receiving portion 72 may also have a depth that is greater than a depth of the second lens receiving portion 74. Such configurations may allow for multiple types of lenses 4 to be secured to the frame 2. For example, a thinner flexible lens (such as the lens 4A) may require greater support by the frame 4. The thinner flexible lens would fit and/or be secured (e.g., via friction fit, snap fit, etc.) within the first lens receiving portion 72. The greater depth of the first lens receiving portion 72 helps provide additional support and/or rigidity to the lens 4 and helps to prevent bending of the lens, thereby improving optical visibility for the wearer through the lens 4.

In some embodiments, the second lens receiving portion 74 has a thickness that is greater than a thickness of the first lens receiving portion 72. The second lens receiving portion 74 may also have a depth that is less than a depth of the first lens receiving portion 72. Such configurations may allow multiple types of lenses 4 to be secured to the frame 2. For example, a thicker, more rigid lens (such as the lens 4B) may be better supported by a thicker and shallower receiving portion of the groove. The thicker, more rigid lens would fit and/or be secured (e.g., via friction fit, snap fit, etc.) within the second lens receiving portion 74. The shallower depth of the second lens receiving portion 74 helps provide additional support to the lens 4 and helps to prevent bending of the lens, thereby improving optical visibility through the lens 4.

Figure 11:
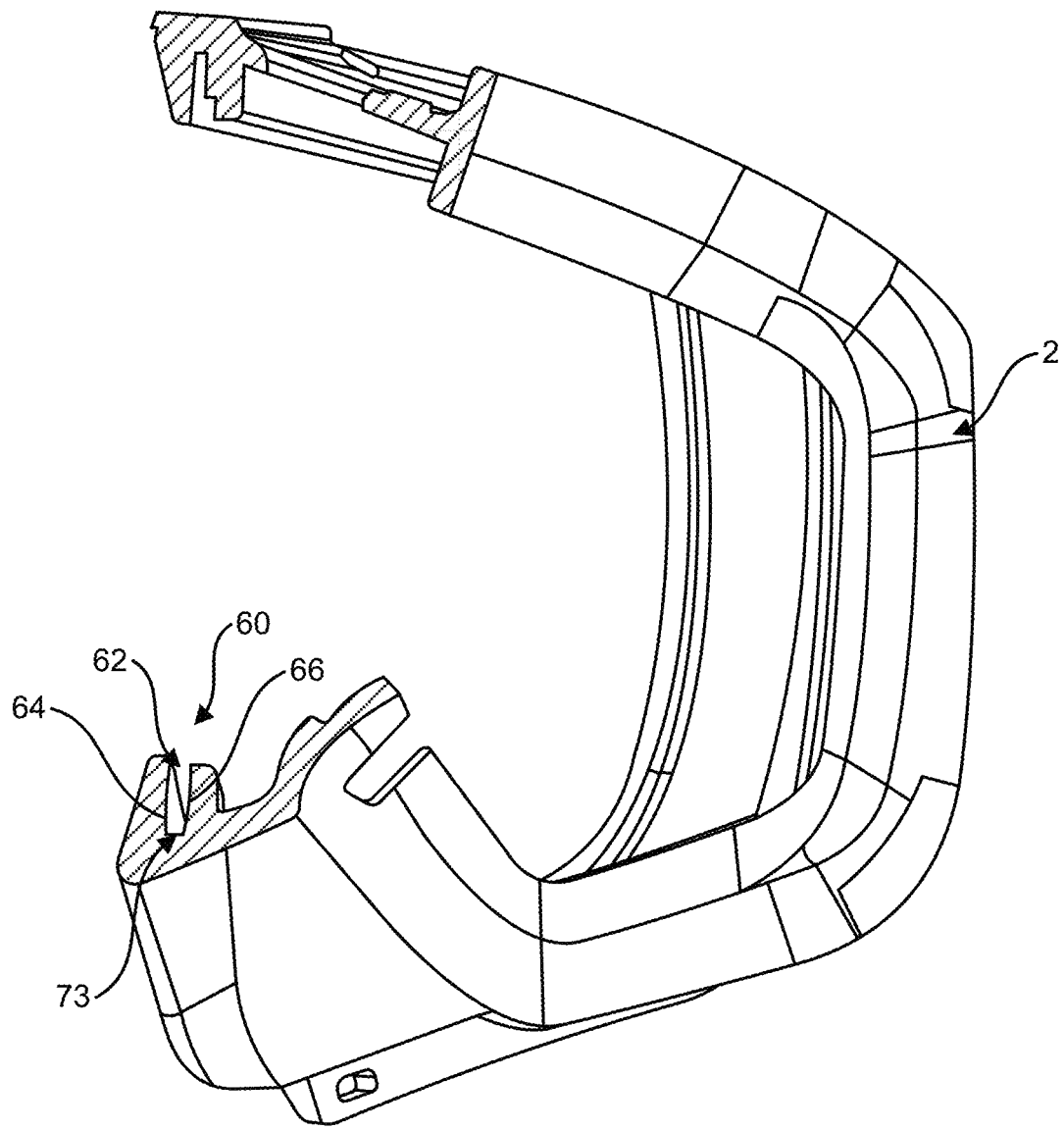
FIG. 11 is a side cross-sectional view of a frame of an eyewear according to some example embodiments.

FIG. 11 illustrates an example cross-sectional view of the frame 2 at an intermediate region of the frame. In some embodiments, the shape of the groove 62 may be uniform along the length of the groove (e.g., the shape of the groove 62 may be similar to the shape described above with respect to FIGS. 10A-10C). In some embodiments, the shape of the groove 62 varies along the length of the groove, which may further help support a variety of types of lenses 4. For example, in some embodiments, the lens 4 (e.g., the second lens 4B) has a variable thickness. The lens 4 may have a lesser thickness and/or be less rigid towards the lateral peripheries of the lens 4. In such circumstances, the frame 2 described herein provides additional support for such lenses near the intermediate region of the frame 2. For example, as shown in FIG. 11, the first lens receiving portion 72 and the second lens receiving portion 74 may form a single receiving portion 73 that may receive at least a portion of various types of lenses (e.g., the first lens 4A and the second lens 4B). The receiving portion 73 may have a depth that is greater than a depth of the second receiving portion 74, for example, to better support the more flexible and/or thinner periphery (or the portion) of the lens 4.

Figure 12:
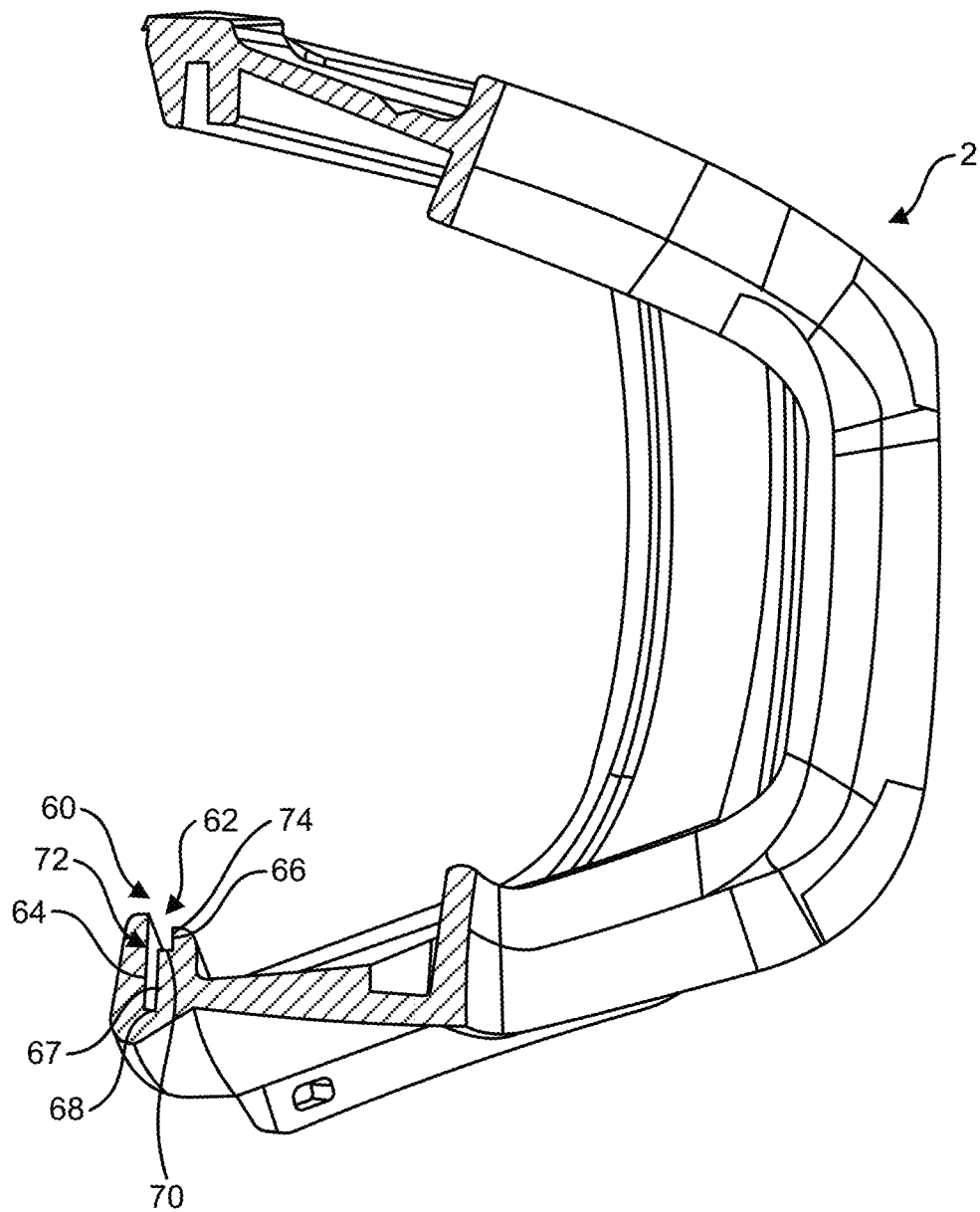
FIG. 12 is a side cross-sectional view of a frame of an eyewear according to some example embodiments.

FIG. 12 illustrates an example cross-sectional view of the groove 62 of the frame 2 towards the periphery of the frame 2. In some embodiments, the groove of the frame 2 near the periphery of the frame 2 has a similar cross-section and shape as the portion of the groove positioned near the nasal region (as described above with respect to FIGS. 10A-10C and 13). In some embodiments, the shape of the groove of the frame 2 near the periphery of the frame 2 is similar to the shape of the groove of the frame 2 near the nasal region of the frame 2, but has a greater depth to provide additional support to certain lenses 4, such as lenses having variable geometries.

As noted above, the frame described herein beneficially supports multiple lens geometries and allows for easier interchangeability of lenses, thereby enhancing the wearer's experience. In some implementations, by providing better support for various types of lenses, the frame may help to improve optical clarity for the wearer, thereby improving eyewear performance.

In some embodiments, the frame including the lens retention system described herein (e.g., the lens retention system 60 having the groove 62) may couple and/or otherwise interchangeably secure multiple types of lenses without the use of pegs, clips, magnets, screws, and/or other types of mechanical fasteners, a clamping mechanism, and the like.

In some embodiments, the eyewear 100 additionally or alternatively includes an attachment system for a light (e.g., a flashlight, an LED light, etc.). The attachment system for the light may be positioned on the first or second outrigger 106, 108, the frame 2, and/or other positions. The attachment system for the light may be configured to receive and hold a light-emitting device (e.g., a flashlight, LEDs, etc.) on the eyewear 100 to illuminate a visible area in front of and/or to the sides of the wearer.

In some embodiments, the eyewear 100 additionally or alternatively includes an attachment system for a camera (e.g., an action camera, a still-photography camera, a GoPro®, etc.). The attachment system for the camera may be positioned on the right or left outriggers 6, 8, the frame 2, and/or other positions. In one embodiment, the attachment system for the camera is positioned on one side of the eyewear 100 to receive and hold a camera device for capturing photos and/or video of the wearer performing some action (e.g., riding a dirt bike, etc.). In other embodiments, the attachment system for the camera is positioned on both sides of the eyewear 100 to receive and hold two camera devices to the eyewear 100. According to an exemplary embodiment, the eyewear 100 having two camera devices attached thereto facilitates three-dimensional and/or virtual filming of the wearer's actions.

In some embodiments, the eyewear 100 additionally or alternatively includes an attachment system for an integrated heads up display (HUD). The attachment system for the HUD may be positioned on the eyewear 100. The attachment system for the HUD may be configured to receive and hold a HUD on the eyewear 100 to provide various information across the lens 4 for viewing by the wearer of the eyewear 100 (e.g., directions, notifications, vehicle information, etc.).

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "upper", "lower", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An eyewear system configured to be worn by a wearer comprising:
   a first lens having a first thickness;
   a second lens having a second thickness different from the first thickness; and
   a frame comprising:
   a lens opening defined by an upper frame portion, a lower frame portion, a first lateral side portion, and a second lateral side portion, the lens opening configured to extend across both eyes of the wearer; and
   a groove surrounding the lens opening, the groove configured to interchangeably receive and secure the first lens or the second lens within the lens opening, wherein the groove comprises
      a first lens receiving portion configured to receive the first lens, the first lens receiving portion having an outer groove wall and an intermediate groove wall defining a first width extending from the outer groove wall to the intermediate groove wall and a first platform having a first depth defined by the length of the outer groove wall, the first depth and the first width defining a first receiving volume; and
      a second lens receiving portion configured to receive the second lens, the second lens receiving portion having the outer groove wall and an inner groove wall defining a second width extending from the outer groove wall to the inner groove wall and a second platform having a second depth defined by the length of the inner groove wall, the second depth and the second width defining a second receiving volume, wherein the first depth is greater than the second depth, wherein the first width is equivalent to a thickness of the first lens and less than the second width, the second width is equivalent to a thickness of the second lens, and the first receiving volume at least partially overlaps with the second receiving volume.

2. The system of claim 1, wherein the first lens has one or more first properties, wherein the second lens has one or more second properties, wherein the one or more first properties are different from the one or more second properties, and wherein the one or more first properties and the one or more second properties comprise lens rigidity and lens material.

3. The system of claim 1, wherein a shape of the groove is constant along a length of the groove.

4. The system of claim 1, wherein a shape of the groove varies along a length of the groove.

5. The system of claim 1, wherein at least a portion of the groove comprises a stepped cross section wherein a first step comprises the first depth and the first width and a second step comprises the second depth, wherein the first depth is greater than the second depth, and a base of the stepped cross section comprises the second width.

6. The system of claim 1, wherein the first lens is disposed in the first lens receiving portion.

7. The system of claim 1, wherein the second lens is disposed in the second lens receiving portion.

8. The system of claim 1, wherein the groove comprises one or more couplers configured to mate with one or more coupling receivers located on the first lens or the second lens.

9. The system of claim 8, wherein the one or more couplers are evenly spaced along a length of the groove.

10. The system of claim 8, wherein the one or more couplers are variably spaced along a length of the groove.

11. The system of claim 8, wherein the one or more coupling receivers extend radially inwardly from an outer edge of the first lens or the second lens.

* * * * *